(12) United States Patent
Niino et al.

(10) Patent No.: US 6,935,186 B2
(45) Date of Patent: Aug. 30, 2005

(54) FATIGUE SAFETY FACTOR TESTING METHOD AND FATIGUE SAFETY FACTOR TESTING APPARATUS

(75) Inventors: Tadashi Niino, Saitama (JP); Hirotaka Murakami, Saitama (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 3 days.

(21) Appl. No.: 10/685,203

(22) Filed: Oct. 14, 2003

(65) Prior Publication Data

US 2004/0079165 A1 Apr. 29, 2004

(30) Foreign Application Priority Data

Oct. 24, 2002 (JP) ........................................ 2002-309268

(51) Int. Cl.[7] ................................................. G01N 3/32
(52) U.S. Cl. ............................................ 73/808; 702/42
(58) Field of Search .......................... 73/804, 805, 808; 702/42

(56) References Cited

U.S. PATENT DOCUMENTS

| | | | | |
|---|---|---|---|---|
| 4,764,882 A | * | 8/1988 | Braschel et al. | ............... 702/42 |
| 6,052,652 A | * | 4/2000 | Lee | ............................. 702/42 |
| 6,212,486 B1 | * | 4/2001 | Huang et al. | ................... 703/7 |

FOREIGN PATENT DOCUMENTS

JP            08-339396           12/1996

* cited by examiner

*Primary Examiner*—Max Noori
(74) *Attorney, Agent, or Firm*—Carrier, Blackman & Associates, P.C.; William D. Blackman; Joseph P. Carrier

(57) ABSTRACT

Although there has been described what is the present embodiment of the invention, it will be understood by persons skilled in the art that variations and modifications may be made thereto without departing from the spirit and scope of the invention set forth in the appended claims.

15 Claims, 5 Drawing Sheets

| MATERIAL | TEMPERATURE | MEAN STRESS | AMPLITUDE STRESS |
|---|---|---|---|
| 17-1 | 17-2 | 17-3 | 17-4 |
|  |  |  |  |

17

| MATERIAL | CONVERSION FUNCTION A | CONVERSION FUNCTION B |
|---|---|---|
| 18-1 | 18-2 | 18-3 |
|  |  |  |

| Node | σ | T |
|---|---|---|
| 1 | 10.3 | 154. |
| 2 | 23.0 | 56. |
| 3 | -4.5 | 230. |
| ... | ... | ... |
| 100000 | 12.8 | 280. |

⇧ $\sigma U = f(\sigma, T)$ S05

| Node | σU |
|---|---|
| 1 | 0.89 |
| 2 | 0.62 |
| 3 | -0.15 |
| ... | ... |
| 100000 | 1.2 |

⇧ CALCULATE FATIGUE SAFETY FACTOR S06

| Node | Saf |
|---|---|
| 1 | 1.2 |
| 2 | 1.4 |
| 3 | 7.2 |
| ... | ... |
| 100000 | 0.8 |

US 6,935,186 B2

FATIGUE SAFETY FACTOR TESTING METHOD AND FATIGUE SAFETY FACTOR TESTING APPARATUS

BACKGROUND OF THE INVENTION

1. Field of the Invention

The present invention relates to a fatigue safety factor testing apparatus and a method of testing a fatigue safety factor, and more particularly to a fatigue safety factor testing apparatus and a method of testing a fatigue safety factor which tests a fatigue safety factor dependent on temperature.

2. Description of the Related Art

A method of calculating a fatigue safety factor of a part using Computer Aided Engineering (hereinafter, to be referred to as "CAE") is known. A calculation program for this purpose is commercially available in which a fatigue limit diagram is calculated to the part consisting of a kind of material under a predetermined condition, e.g., a predetermined temperature. Here, the fatigue limit diagram is a graph showing relationship between mean stress permissible to an object to be tested and permissible amplitude stress.

When only the fatigue limit diagram calculated under the predetermined condition can be used, it is difficult to accurately estimate an actual fatigue limit of the part in case of different conditions, e.g., different temperature depending on the location of the part. A component of an engine of a vehicle such as a piston is exemplified as such a part. In case of the piston, the piston moves in up and down directions in accordance with explosion in an engine cylinder at high speed, and the temperature is different largely depending on a portion of the piston.

Also, when the fatigue limit of the part can not be estimated precisely, it is not possible to estimate the fatigue safety factor of the part correctly. Therefore, the safety has the first priority and a very high safety factor is set. As a result, this leads the increase of weight of the engine, the increase of material cost and so on, resulting in increase of the environment load. Thus, the technique is demanded that can calculate the fatigue safety factor of each part at high speed and correctly through an automatic process based on the temperature and stress of every portion.

In conjunction with the above description, a processor for a numerical value simulation of a deformation process of a metal plate is disclosed in Japanese Laid Open Patent Application (JP-A-Heisei 8-339396). This conventional processor has an input section, a rapture limit distortion/wrinkle limit stress data storage section, a rapture/wrinkle margin calculating section, a rapture/wrinkle margin data storage section and an output section. The input section stores distortion/stress data of each element obtained from the numerical value simulation of a plastic deformation process of the metal plate using a finite-element method in the distortion/stress data storage section. The rapture limit distortion/wrinkle limit stress data storage section stores rapture limit distortion/wrinkle limit stress data. The rapture/wrinkle margin calculating section calculates a rapture/wrinkle margin of each element from the rapture limit distortion/wrinkle limit stress data and distortion/stress data of each element. The rapture/wrinkle margin data storage section stores the calculated rapture/wrinkle margin of each element. Then, the output section outputs a contour line distribution of the rapture/wrinkle margin.

SUMMARY OF THE INVENTION

Therefore, an object of the present invention is to provide a fatigue safety factor testing apparatus and a method of testing a fatigue safety factor, in which the fatigue safety factor of each part can be calculated at high speed and correctly through an automatic process based on temperature and stress of every portion of the part which are measured or calculated.

Also, another purpose of the present invention is to provide a fatigue safety factor testing apparatus and a method of testing a fatigue safety factor, in which a fatigue limit diagram is calculated which does not depend on material and temperature of a part and a fatigue safety factor of the part can be easily calculated.

Also, another purpose of the present invention is to provide a fatigue safety factor testing apparatus and a method of testing a fatigue safety factor, in which it is possible to improve the efficiency of design and development, and a cost for them can be reduced.

In an aspect of the present invention, a fatigue safety factor testing apparatus includes a FEM calculating section, a normalized stress calculating section and a fatigue safety factor calculating section. The FEM calculating section carries out a FEM calculation to meshes of a part to calculate a stress of each of the meshes of the part. The normalized stress calculating section calculates a normalized stress of a stress applied to each of the meshes with respect to a fatigue limit as a function of a temperature and material of each of the meshes. The fatigue safety factor calculating section calculates a fatigue safety factor of each of the meshes based on a normalized fatigue limit obtained by normalizing the fatigue limit and the normalized stress.

Here, the normalized stress and the normalized fatigue limit may be independent from the temperature and material of each of the meshes of the part, or may be independent from the temperature of each of the meshes of the part.

Also, the fatigue safety factor testing apparatus may further include a function table which stores a conversion function as a function of the temperature and the material. The normalized stress calculating section refers to the function table based on the material of each of the meshes of the part to acquire the conversion function, and normalizes the stress applied to each of the meshes of the part using the conversion function. In this case, the fatigue safety factor testing apparatus may further include a stress data table which has the fatigue limit as a function of the material and the temperature, and a conversion function generating section which generates the conversion function based on the fatigue limit for every temperature, and stores the generated conversion function in the function table. In this case, the conversion function generating section may generate the normalized fatigue limit in addition to the conversion function and stores the normalized fatigue limit in the stress data table in relation to the material. The fatigue safety factor calculating section may refer to the stress data table based on a material of each of the meshes of the part to acquire the normalized fatigue limit.

Also, the fatigue safety factor testing apparatus may further include a display section which displays each of the meshes of the part in a color corresponding to the fatigue safety factor.

In another aspect of the present invention, fatigue safety factor testing apparatus include a normalized stress calculating section and a fatigue safety factor calculating section. The normalized stress calculating section normalizes a stress applied to a part using a conversion function for converting fatigue limit for every temperature of the part and for every material of the part into a normalized fatigue limit which does not depend on the temperature and outputs as a normalized stress. The fatigue safety factor calculating section calculates a fatigue safety factor of the part based on the normalized fatigue limit and the normalized stress.

Here, the fatigue safety factor testing apparatus may further include a function table which stores the conversion function. The normalized stress calculating section refers to the function table based on a material of each of the meshes of the part to acquire the conversion function. The fatigue safety factor testing apparatus may further include a stress data table which has the fatigue limit for every temperature and for every material, and a conversion function generating section which generates the conversion function based on the fatigue limit for every temperature and for every material, and stores the generated conversion function in the function table.

Also, the stress is at least one of mean stress and amplitude stress applied to the part, and the fatigue limit shows a permissible mean stress and a permissive amplitude stress.

In another aspect of the present invention, a method of testing a fatigue safety factor is achieved by (a) acquiring a stress applied to each of meshes of a part; by (b) normalizing the stress using a conversion function for converting fatigue limit for a material of each of meshes of a part and for every temperature into a normalized fatigue limit which does not depend on the temperature; and by (c) calculating the fatigue safety factor of each of the meshes of the part based on the normalized fatigue limit obtained by normalizing the fatigue limit using the conversion function and the normalized stress.

The method may further include (d) determining the conversion function through the normalization of the fatigue limit.

Also, the stress may be at least one of mean stress and amplitude stress applied to the part, and the fatigue limit shows a permissible mean stress and a permissive amplitude stress.

Also, the method may further include displaying each of the meshes of the part in a color corresponding to the fatigue safety factor.

In another aspect of the present invention, a software product executed by a computer and recording codes of a method comprising the steps of (a) acquiring a stress applied to each of meshes of a part; (b) normalizing the stress using a conversion function for converting fatigue limit for a material of each of meshes of a part and for every temperature into a normalized fatigue limit which does not depend on the temperature; and (c) calculating the fatigue safety factor of each of the meshes of the part based on the normalized fatigue limit obtained by normalizing the fatigue limit using the conversion function and the normalized stress.

In accordance with the software product, the method may further include (d) determining the conversion function through the normalization of the fatigue limit.

Also, the stress is at least one of mean stress and amplitude stress applied to the part, and the fatigue limit shows a permissible mean stress and a permissive amplitude stress.

Also, in the software product, the method may further include displaying each of the meshes of the part in a color corresponding to the fatigue safety factor.

BRIEF DESCRIPTION OF THE DRAWINGS

FIGS. 7A to 7C are diagrams showing the conversion results of tetra mesh data.

DESCRIPTION OF THE PREFERRED EMBODIMENTS

Hereinafter, a fatigue safety factor testing apparatus of the present invention will be described with reference to the attached drawings. In the following, the fatigue safety factor testing apparatus used for engine design of a vehicle will be described as an example, but the present invention is not limited to it and is applicable to the design and development of other buildings and structures.

Figure 1:
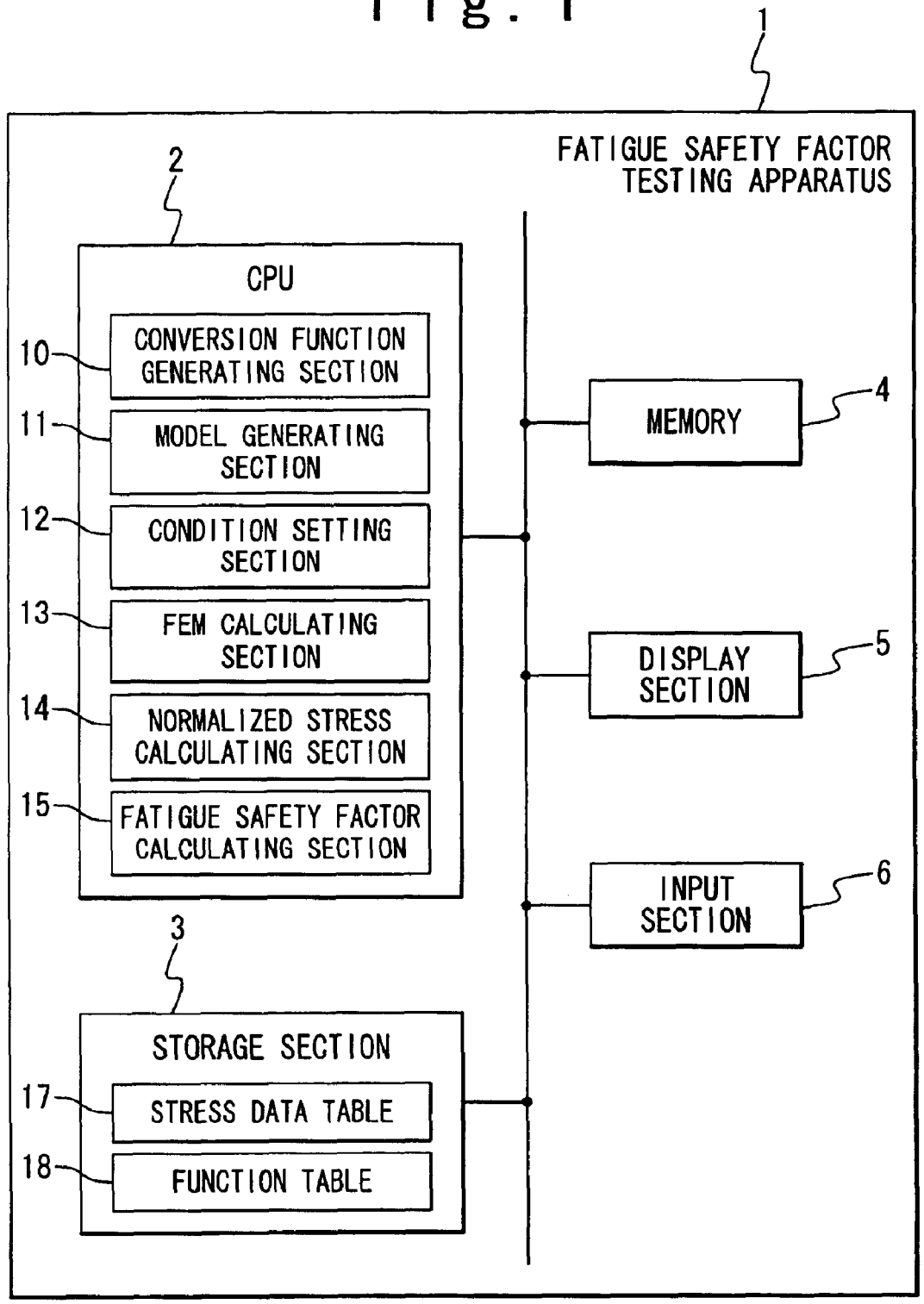
FIG. 1 is a diagram showing the structure of a fatigue safety factor testing apparatus according to an embodiment of the present invention.

The structure of the fatigue safety factor testing apparatus according to an embodiment of the present invention will be described with reference to FIG. 1. As shown in FIG. 1, the fatigue safety factor testing apparatus 1 according to the embodiment of the present invention is an information processing apparatus such as a work station and a personal computer. The fatigue safety factor testing apparatus 1 is composed of a CPU 2, a storage section 3 such as a hard disk, a memory 4 such as a RAM, a display section 5, and an input section 6 such as a keyboard and a mouse.

In the fatigue safety factor testing apparatus 1, the CPU contains a conversion function generating section 10, a model generating section 11, a condition setting section 12, an FEM calculating section 13, a normalized stress calculating section 14, and a fatigue safety factor calculating section 15. All of them are realized as sections for executing a series of programs stored in the storage section 3.

Also, the storage section 3 stores a stress data table 17 and a function table 18. The stress data table 17 stores relationship data of a kind of material and a fatigue limit diagram indicating relationship between mean stress and amplitude stress. The function table 18 stores relationship data of a kind of material and conversion functions for normalizing and converting the fatigue limit diagram to the material for every temperature into the normalized fatigue limit diagram independent from temperature and material.

The conversion function generating section 10 executes a software program and generates a conversion function A and a conversion function B from a fatigue limit diagram for a kind of material stored in the stress data table 17 and stores the same in the function table 18. The conversion functions A and B are used to generate the normalized fatigue limit diagram.

The model generating section 11 supports the design of a three-dimensional (hereinafter, to be also referred to as "3D") model of an engine as an object of structural analysis. The model generating section 11 is a section for executing a CAD (Computer Aided Design) software program, for example. The conventional CAD software program can be used.

The condition setting section 12 executes a software program and sets conditions about the engine as the object of the structural analysis. The conditions are used in FEM calculation. The conditions contain engine operation conditions such as speed, acceleration and torque, and engine specifications such as a rotation frequency, horsepower, and a pressure in a cylinder.

The FEM calculating section 13 converts the above-mentioned three-dimensional model into an FEM model. Then, the FEM calculating section 13 carries out FEM calculation for the FEM analysis to the FEM model under the above conditions. The FEM calculating section 13 is a section for executing an FEM software program, for example.

The normalized stress calculating section 14 executes a software program and normalizes the stress applied to a part by using the fatigue limit diagram for the material of the part for every temperature of the part and outputs a normalized stress. That is, the stress of the fatigue limit diagram corresponds to the normalized stress of the normalized fatigue limit diagram.

The fatigue safety factor calculating section 15 executes a software program and calculates a fatigue safety factor of the part based on the normalized fatigue limit diagram and the normalized stress calculated by the normalized stress calculating section 14.

Figure 2:
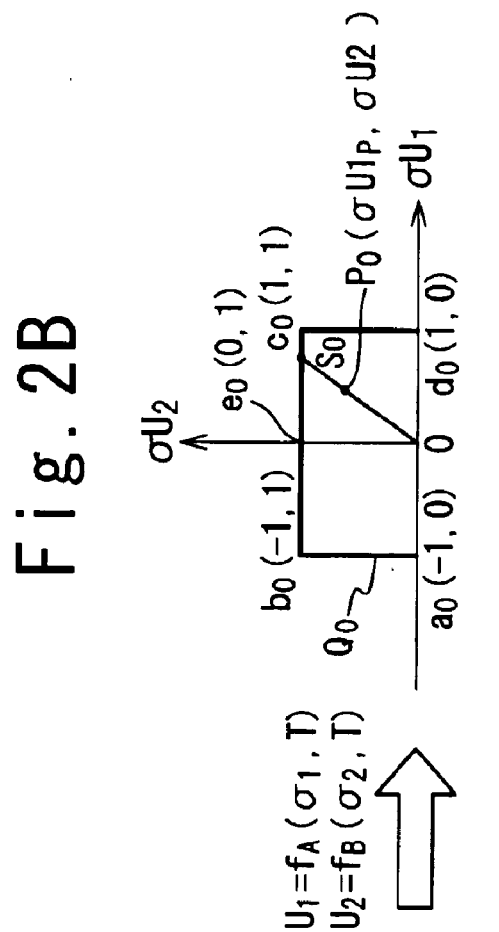
FIGS. 2A and 2B are graphs showing examples of a fatigue limit diagram and a normalized fatigue limit diagram obtained.

The fatigue limit diagram and the normalized fatigue limit diagram used in the fatigue safety factor testing apparatus of the present invention will be described. FIGS. 2A and 2B are graphs showing examples of a fatigue limit diagram of some material and a normalized fatigue limit diagram obtained by normalizing it. FIG. 2A shows a fatigue limit diagram and FIG. 2B shows the normalized fatigue limit diagram.

In the fatigue limit diagram shown in FIG. 2A, the horizontal axis is mean stress $\sigma 1$ and the vertical axis shows amplitude stress $\sigma 2$. A curve $Q_1$ (point $a_1$-point $b_1$-point $e_1$-point $c_1$-point $d_1$), a curve $Q_2$ (point $a_2$-point $b_2$-point $e_2$-point $c_2$-point $d_2$), and a curve $Q_3$ (point $a_3$-point $b_3$-point $e_3$-point $c_3$-point $d_3$) are the fatigue limit diagram at the room temperature (24° C.), 100° C., and 200° C., respectively. The fatigue limit diagram is a graph showing a value of the fatigue limit for every temperature, and is generally determined depending on the material but the profile is different. FIG. 2A is only an example. Also, in the temperature range in which the engine is used, the profile becomes smaller in size similarly with the increase of the temperature (the curve $Q_1$ to the curve $Q_2$, to the curve $Q_3$).

The calculation of the fatigue limit diagram is complicated because the profile depends on the material and the temperature. Therefore, in the present invention, the normalized fatigue limit diagram as shown in FIG. 2B is introduced. The normalized fatigue limit diagram is obtained by normalizing mean stress and amplitude stress $\sigma 2$ by using the fatigue limits in the temperature. In the normalized fatigue limit diagram, the horizontal axis is normalized mean stress $\sigma U1$ obtained by normalizing the mean stress $\sigma 1$, and the vertical axis is normalized amplitude stress $\sigma U2$ obtained by normalizing the amplitude stress $\sigma 2$. The curves $Q_1$ to $Q_3$ of the fatigue limit diagram are all converted into a curve $Q_0$. That is, the points $a_1$ to $a_3$ of the curves $Q_1$ to $Q_3$ are converted into the point $a_0(-1, 0)$. The points $b_1$ to $b_3$ are converted into the point $b_0(-1, 1)$. The points $e_1$ to $e_3$ are converted into the point $e_0(0, 1)$. The points $c_1$ to $c_3$ are converted into the point $c_0(1, 1)$. The points $d_1$ to $d_3$ are converted into the point $d_0(1, 0)$. The point P on the fatigue limit diagram in case of T=24° C. becomes the point $P_0$ on the normalized fatigue limit diagram. Thus, the normalized fatigue limit diagram does not depend on the material and temperature and becomes the curve $Q_0$.

In this way, the stress $\sigma$ is normalized and becomes a dimensionless quantity. The manipulation becomes easy in case of fatigue safety calculation and calculation using the mean stress and the amplitude stress between different kinds of materials and different temperatures.

The conversion function f is used for the conversion from the fatigue limit diagram into the normalized fatigue limit diagram. For example, as for the point $P(\sigma 1_P, \sigma 2_P)$, elements are converted into $\sigma U1_P=f_A(\sigma 1_P, T)$ and $\sigma U2_P=f_B(\sigma 2_P, T)$, and the point $P(\sigma 1_P, \sigma 2_P)$ is converted into a point $P_0(\sigma U1_P, \sigma U2_P)$. Because the fatigue limit diagram is not constant and is different depending on a kind of the material and temperature, the material conversion function $f(\sigma, T)(f_A(\sigma 1,T), f_B(\sigma 2,T))$ is set for every kind of material.

The conversion function f is generated as follows. First, the curve Q and each point P on the fatigue limit diagram are converted into a curve and points on the polar coordinate system. That is, a point $S(\sigma 1_0, \sigma 2_0)$ on the curve Q and the point $P(\sigma 1_P, \sigma 2_P)$ on the graph are converted into a point $S(r_0, \theta_0)$ for the polar coordinate system and a point $P(r_P, \theta_P)$ on the polar coordinate system. Here, $\sigma 1_{0,P}=r_{0,P} \cdot \cos\theta_{0,P}$, $\sigma 2_{0,P}=r_{0,P} \cdot \sin\theta_{0,P}$. Then, the curve Q (point S) on the fatigue limit diagram is converted into the curve $Q_0$ (point $S_0$) on the normalized fatigue limit diagram. In this case, $\theta_0$ is not changed just as it is, and a coefficient k to $r_0$ is determined such that the point S on the curve Q is mapped the point $S_0$ on the curve $Q_0$. As a result, the point S is mapped to the point $S_0(k \cdot r_0, \theta_0)$ on the curve $Q_0$. Then, the point P is mapped into the point $P_0(k \cdot r, \theta)$ on the normalized fatigue limit diagram using the value k.

As known, the fatigue limit diagram becomes smaller similarly while keeping the shape as the temperature increases. Therefore, a coefficient q(T) is determined which becomes larger when temperature T becomes higher from a reference temperature $T_0$ and becomes smaller when temperature T becomes lower from the reference temperature $T_0$. The coefficient q(T) is determined from the fatigue limit diagram for every material. That is, the point $P(\sigma 1_P, \sigma 2_P)$ is mapped into a point $P_0(q(T) \cdot k \cdot r, q(T) \cdot \theta)$ on the polar coordinate system and the point $P_0(\sigma U1_P, \sigma U2_P)$ in the $\sigma 1$-$\sigma 2$ coordinate system. From this, $$\sigma U1_P = f_A(\sigma 1_P, T)$$
$$= q(T) \cdot k \cdot r \cdot \cos\theta$$
$$= q(T) \cdot k \cdot (\sigma 1^2 + \sigma 2^2)^{1/2} \cdot \sigma 1 \cdot (\sigma 1^2 + \sigma 2^2)^{-1/2}$$

$$\sigma U2_P = f_B(\sigma 2_P, T)$$
$$= q(T) \cdot k \cdot r \cdot \sin\theta$$
$$= q(T) \cdot k \cdot (\sigma 1^2 + \sigma 2^2)^{1/2} \cdot \sigma 2 \cdot (\sigma 1^2 + \sigma 2^2)^{-1/2}$$

where $r=(\sigma 1^2+\sigma 2^2)^{1/2}$
$\cos\theta=\sigma 1 \cdot (\sigma 1^2+\sigma 2^2)^{-1/2}$
$\sin\theta=\sigma 2 \cdot (\sigma 1^2+\sigma 2^2)^{-1/2}$ It should be noted that the conversion function f of the present invention is not limited to the above example. Any type of conversion function may be used if it is possible to convert the fatigue limit diagram into the graph shown in FIG. 2B.

Figures 3, 4, 5:
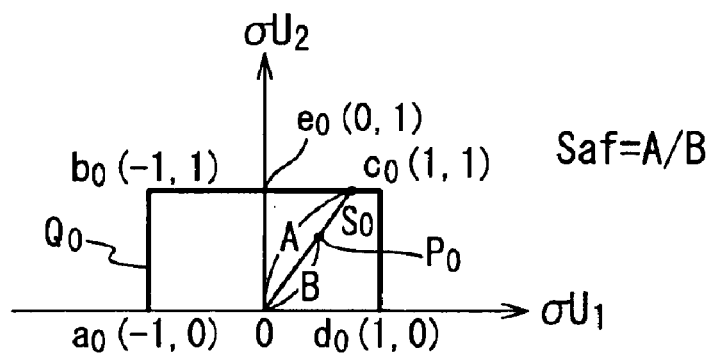
FIG. 3 is a diagram showing a method of calculating the fatigue safety factor by using the normalized fatigue limit diagram.
FIG. 4 is a diagram showing a stress data table.
FIG. 5 is a diagram showing a function table.

Next, the method of calculating the fatigue safety factor using the above-mentioned normalized fatigue limit diagram will be described. FIG. 3 is a diagram showing the method of calculating the fatigue safety factor using the normalized fatigue limit diagram. The normalized fatigue limit diagram shown here is the same as a graph shown in FIG. 2B. In FIG. 3, a fatigue safety factor (Saf) to the point $P_0$ is a ratio of the distance B from the origin point O to the point $P_0$ to the distance A from the origin point O of the graph to the point $S_0$. That is, Saf=A/B. Here, the point $S_0$ is an intersection point of the straight line $OP_0$ and the curve $Q_0$.

Next, the stress data table 17 of storage section 3 will be described. FIG. 4 is a diagram showing the stress data table 17. The stress data table 17 stores relationship data of a kind of the material and a fatigue limit diagram showing the relationship between the mean stress and the amplitude stress. The stress data table 17 has fields of material 17-1, temperature 17-2, mean stress 17-3, and amplitude stress 17-4. The material field 17-1 stores a kind of material, and contains a case of different states in the same kind of material. The temperature field 17-2 stores the temperature of the material. The means stress field 17-3 and the amplitude stress field 17-4 store relations of the mean stress and the amplitude stress in case of the material in the material field 17-1 and the temperature in the temperature field 17-2.

The stress data table 17 corresponds to the graph shown in FIG. 2A. It is not necessary to prepare many temperature data as data in the temperature field 17-2 for every material. It is sufficient to prepare the temperature data for the temperatures of 20° C., 50° C. and 100° C. Thus, the number of data to be stored can be restrained.

FIG. 5 is a diagram showing the function table 18. The function table 18 stores relationship data of a kind of the material and the conversion functions. The material field 18-1 is the same as the material field 17-1. The conversion function A 18-2 and the conversion function B 18-3 are functions used to convert or map data on the fatigue limit diagram into the data on the normalized fatigue limit diagram. The conversion function A 18-2 is for mean stress σ1 and the conversion function B 18-3 is for amplitude stress σ2. The details are already described referring to FIGS. 2A and 2B. For example, in the examples shown in FIGS. 2A and 2B, the conversion function A 18-2 is $f_A(\sigma1, T) = q(T) \cdot k \cdot (\sigma1^2 + \sigma2^2)^{1/2} \cdot \sigma1 \cdot (\sigma1^2 + \sigma2^2)^{-1/2}$, and the conversion function B 18-3 is $f_B(\sigma2, T) = q(T) \cdot k \cdot (\sigma1^2 + \sigma2^2)^{1/2} \cdot \sigma2 \cdot (\sigma1^2 + \sigma2^2)^{-1/2}$. It should be noted that the conversion function A 18-2 and the conversion function B 18-3 are generated by the conversion function generating section 10 and are stored in the function table 18. However, they may be previously prepared. In this case, a part of the following calculation process can be omitted.

Figure 6:
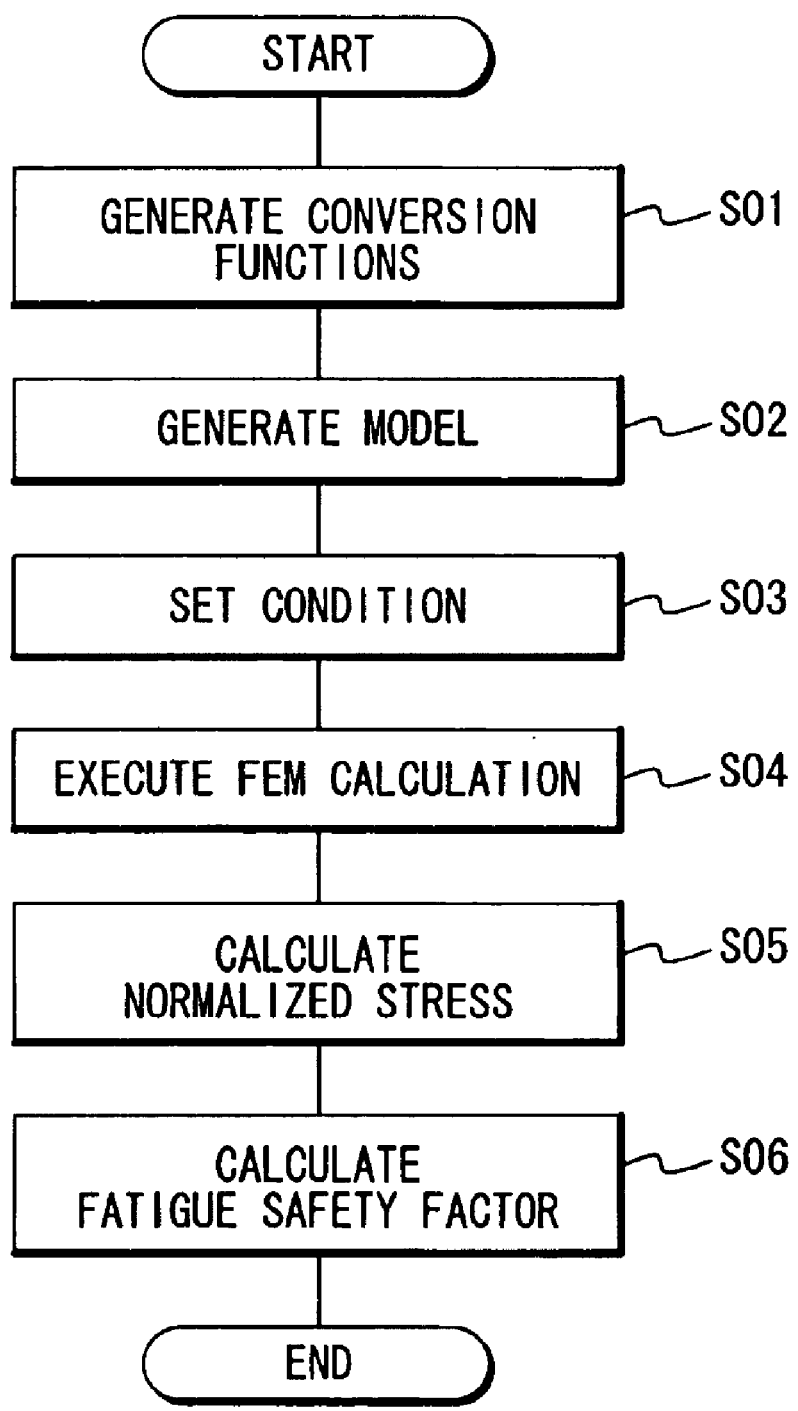
FIG. 6 is a flow chart showing the operation of the fatigue safety factor testing apparatus according to the embodiment of the present invention.

Next, an operation of the fatigue safety factor testing apparatus according to the embodiment of the present invention will be described. FIG. 6 is a flow chart showing the operation of the fatigue safety factor testing apparatus according to the embodiment of the present invention.

(1) Step S01

The designer selects a material relating to the CAE analysis. The conversion function generating section 10 generates the conversion function A and the conversion function B for the material based on the stress data base 17 (material 17-1, temperature 17-2, mean stress 17-3 and amplitude stress 17-4 of a fatigue limit diagram) and stores it in the function table 18. That is, the conversion function generating section 10 generates the conversion functions $f_A(\sigma, T)$ and $f_B(\sigma, T)$ which are used to generate a graph shown in FIG. 2B from the graph shown in FIG. 2A and stores them in the function table 18 as the conversion function A and the conversion function B, respectively. Also, the normalized fatigue limit diagram obtained at this time may be stored in the stress data table 17.

(2) Step S02

The designer designs a three-dimensional model of an engine as an object of the structural analysis using the model generating section 11.

(3) Step S03

The designer sets conditions of the engine as the object of the structural analysis using the condition setting section 12. The conditions are operation conditions of the engine and specifications of the engine, such as rotation frequency, horsepower, and cylinder internal pressure.

(4) Step S04

The FEM calculating section 13 converts the above-mentioned three-dimensional model into a FEM model. Then, FEM calculation is carried out for the FEM analysis to the FEM model under the above conditions. The FEM calculating section 13 carries out two kinds of analyses A and B.

A: The temperature of each section of the FEM model with a tetra mesh structure is calculated.

B: The stresses such as mean stress and amplitude stress at each section of the FEM model with the tetra mesh structure are calculated.

(5) Step S05

The normalized stress calculating section 14 normalizes each of the stresses of a part of the engine calculated at the step S04. At this time, the fatigue limit diagram and the conversion functions f (the conversion function A 18-2 and the conversion function B 18-3 corresponding to the material 18-1 of the part) stored in the function table 18 for temperature and material of the part are used. When the normalized fatigue limit diagram is stored, the normalized fatigue limit diagram and the conversion functions f may be used. Then, the normalized stress calculating section 14 outputs the conversion result as the normalized stresses.

(6) Step S06

The fatigue safety factor calculating section 15 calculates the fatigue safety factor of the part based on the normalized fatigue limit diagram calculated from the fatigue limit diagram using the conversion functions stored in the stress data table 17 and the normalized stresses calculated at the step S05 by the method described with reference to FIG. 3. Then, the fatigue safety factor calculating section 15 controls the display section 5 to display each of tetra meshes in the color corresponding to a value of the calculated fatigue safety factor.

The fatigue safety factor becomes able to be easily calculated by using the normalized fatigue limit diagram. Also, because each tetra mesh is displayed in the color corresponding to the fatigue safety factor, the fatigue safety factor is easy to grasp as the whole of part. Also, the fatigue safety factor becomes able to be grasped visually and objectively.

Here, the data about each of the tetra meshes in the step S05 and the step S06 will be further explained. FIGS. 7A to 7C are diagrams showing the data of each of the tetra meshes in the steps S04 to S06. Sheets 21 to 23 show data in the steps S04 to S06, respectively. In each sheet, Node is an identification number which distinguishes each of the plurality of tetra meshes in the FEM model, and σ, T, σU and Saf are the stress, the temperature, the normalized stress and the safety factor in each of the tetra meshes, respectively (only the amplitude stress is shown in FIGS. 7A to 7C as the stress and the normalized stress). The FEM analysis is accomplished at the step S04 and the relationship between σ and T for every tetra mesh is obtained as shown by the sheet 21 shown in FIG. 7A. Next, the calculation (σU=f(σ, T)) of the normalized stress is accomplished at the step S05 by using the conversion functions f about each data, and σU for each of the tetra meshes is obtained as shown by the sheet 22 of FIG. 7B. Then, the calculation (Saf=A/B) of the fatigue safety factor is accomplished at step S06 and the fatigue safety factor Saf for each of the tetra meshes is obtained as shown by the sheet 23 FIG. 7C.

The stress data table 17 may store the fatigue limit diagram for every temperature and every material. In this case, however, an amount of data to be stored increases more as the kind of the material and the temperature increases more. As a result, the system infrastructure becomes enormous and the access time also increases.

On the other hand, in the present invention, the stress data table 17 does not have data for every temperature and every material and the normalized fatigue limit function is calculated using the conversion functions f. Therefore, the present invention needs not to have a large-scale data and the increase of the system can be restrained.

Also, in the present invention, the curve $Q_0$ of the normalized fatigue limit diagram has the fatigue limit value of "1". Therefore, the fatigue safety factor can be easily grasped numerically through the comparison with the curve $Q_0$.

In this way, in the present invention, the fatigue limit diagram which does not depend on the temperature and the material is calculated by normalizing the fatigue limit diagram which depends on the temperature and material. Therefore, the data of the stress can be easily treated.

By the present invention, the evaluation of the fatigue safety factor of a part or unit using the CAE calculation becomes possible in the design conception step. Because the quality in the initial design of the part or unit improves, faults in a durable examination decrease largely and the cost can be reduced in the design and the development.

According to the present invention, the fatigue safety factor of each part can be calculated at high speed and correctly through the automatic process, and it is possible to improve the efficiency of the design and development.

What is claimed is:

1. A fatigue safety factor testing apparatus comprising:
   a FEM calculating section which carries out a FEM calculation to meshes of a part to calculate a stress of each of said meshes of said part;
   a normalized stress calculating section which calculates a normalized stress of a stress applied to each of said meshes with respect to a fatigue limit as a function of a temperature and material of each of said meshes; and
   a fatigue safety factor calculating section which calculates a fatigue safety factor of each of said meshes based on a normalized fatigue limit obtained by normalizing said fatigue limit and said normalized stress.

2. The fatigue safety factor testing apparatus according to claim 1, wherein said normalized stress and said normalized fatigue limit are independent from the temperature and material of each of said meshes of said part.

3. The fatigue safety factor testing apparatus according to claim 1, wherein said normalized stress and said normalized fatigue limit are independent from the temperature of each of said meshes of said part.

4. The fatigue safety factor testing apparatus according to claim 1, further comprising:
   a function table which stores a conversion function as a function of the temperature and the material, and
   wherein said normalized stress calculating section refers to said function table based on the material of each of said meshes of said part to acquire said conversion function, and normalizes said stress applied to each of said meshes of said part using said conversion function.

5. The fatigue safety factor testing apparatus according to claim 4, further comprising:
   a stress data table which stores said fatigue limit as a function of the material and the temperature; and
   a conversion function generating section which generates said conversion function based on said fatigue limit for multiple temperatures, and stores the generated conversion function in said function table.

6. The fatigue safety factor testing apparatus according to claim 5, wherein said conversion function generating section generates said normalized fatigue limit in addition to said conversion function and stores said normalized fatigue limit in said stress data table in relation to said material, and
   wherein said fatigue safety factor calculating section refers to said stress data table based on a material of each of said meshes of said part to acquire said normalized fatigue limit.

7. The fatigue safety factor testing apparatus according to claim 1, further comprising:
   a display section which displays each of said meshes of said part in a color corresponding to said fatigue safety factor.

8. A fatigue safety factor testing apparatus comprising:
   a normalized stress calculating section which normalizes a stress applied to a part using a conversion function for converting a fatigue limit for every temperature of said part and for every material of said part into a normalized fatigue limit which does not depend on the temperature and outputs a normalized stress; and
   a fatigue safety factor calculating section which calculates a fatigue safety factor of said part based on said normalized fatigue limit and said normalized stress.

9. The fatigue safety factor testing apparatus according to claim 8, further comprising:
   a function table which stores said conversion function, and
   wherein said normalized stress calculating section refers to said function table based on a material of each of a plurality of meshes of said part to acquire said conversion function.

10. The fatigue safety factor testing apparatus according to claim 9, further comprising:
    a stress data table which stores said fatigue limit for multiple temperatures and said every material of said part;
    a conversion function generating section which generates said conversion function based on said fatigue limit for each of said temperatures and said every material of said part, and stores the generated conversion function in said function table.

11. The fatigue safety factor testing apparatus according to claims 8, wherein said stress is at least one of mean stress and amplitude stress applied to said part, and
    said fatigue limit shows a permissible mean stress and a permissive amplitude stress.

12. A method of testing a fatigue safety factor comprising the steps of:
    (a) acquiring a stress applied to each of meshes of a part;
    (b) normalizing said stress using a conversion function for converting fatigue limit for a material of each of meshes of a part and for multiple temperatures into a normalized fatigue limit which does not depend on the temperature; and
    (c) calculating a fatigue safety factor of each of said meshes of said part based on said normalized fatigue limit obtained by normalizing said fatigue limit using said conversion function and said normalized stress.

13. The method of testing a fatigue safety factor according to claim 12, further comprising the step of:
    (d) determining said conversion function through the normalization of said fatigue limit.

14. The method of testing a fatigue safety factor according to claims 12, wherein said stress is at least one of mean stress and amplitude stress applied to said part, and
    said fatigue limit shows a permissible mean stress and a permissive amplitude stress.

15. The method of testing a fatigue safety factor according to claim 12, further comprising the step of:
    displaying each of said meshes of said part in a color corresponding to said fatigue safety factor.

* * * * *

UNITED STATES PATENT AND TRADEMARK OFFICE
CERTIFICATE OF CORRECTION

PATENT NO.   : 6,935,186 B2
DATED        : August 30, 2005
INVENTOR(S)  : Tadashi Niino and Hirotaka Murakami It is certified that error appears in the above-identified patent and that said Letters Patent is hereby corrected as shown below:

Column 9,
Line 9, insert paragraph:
-- Although there has been described what is the present embodiment of the invention, it will be understood by persons skilled in the art that variations and modifications may be made thereto without departing from the spirit and scope of the invention set forth in the appended claims --.

Signed and Sealed this

Twenty-eighth Day of February, 2006

JON W. DUDAS
*Director of the United States Patent and Trademark Office*